(12) United States Patent
Farra

(10) Patent No.: US 10,427,153 B2
(45) Date of Patent: Oct. 1, 2019

(54) SYSTEMS AND METHODS FOR SEALING A PLURALITY OF RESERVOIRS OF A MICROCHIP ELEMENT WITH A SEALING GRID

(71) Applicant: Microchips Biotech, Inc., Lexington, MA (US)

(72) Inventor: Robert Farra, Acton, MA (US)

(73) Assignee: Microchips Biotech, Inc., Lexington, MA (US)

( * ) Notice: Subject to any disclaimer, the term of this patent is extended or adjusted under 35 U.S.C. 154(b) by 10 days.

(21) Appl. No.: 15/241,581

(22) Filed: Aug. 19, 2016

(65) Prior Publication Data

US 2016/0354780 A1 Dec. 8, 2016

Related U.S. Application Data

(63) Continuation-in-part of application No. 13/595,492, filed on Aug. 27, 2012.
(Continued)

(51) Int. Cl.
*B01L 3/00* (2006.01)
*A61M 31/00* (2006.01)
(Continued)

(52) U.S. Cl.
CPC ........ *B01L 3/502707* (2013.01); *A61B 5/076* (2013.01); *A61B 5/4839* (2013.01); *A61B 5/6861* (2013.01); *A61K 9/0097* (2013.01); *A61M 31/002* (2013.01); *B01L 3/502715* (2013.01); *A61B 2562/12* (2013.01);
(Continued)

(58) Field of Classification Search
CPC ........ A61K 9/0097; A61M 2205/0244; A61M 31/002; A61M 5/172
See application file for complete search history.

(56) References Cited

U.S. PATENT DOCUMENTS 5,782,891 A 7/1998 Hassler et al.
6,052,623 A 4/2000 Fenner et al.
(Continued)

FOREIGN PATENT DOCUMENTS

| EP | 1540727 B1 | 10/2010 |
|----|------------|---------|
| WO | 2012019083 A2 | 2/2012 |
| WO | 2012027137 A1 | 3/2012 |

*Primary Examiner* — Emily L Schmidt
(74) *Attorney, Agent, or Firm* — Eversheds Sutherland (US) LLP

(57) ABSTRACT

Systems and methods for sealing a plurality of reservoirs of a microchip element with a sealing grid are provided. For example, in one embodiment, a microchip element comprises a primary substrate having a plurality of reservoirs defined therein. The microchip element also includes a single continuous sealing groove defined in the primary substrate that extends around each of the plurality of reservoirs. In addition, the microchip element includes a sealing substrate comprising a single continuous sealing protrusion extending therefrom. The single continuous sealing protrusion corresponds to and is configured to mate with the single continuous sealing groove to form a hermetic bond between the primary substrate and the sealing substrate. In this manner, the single continuous sealing groove and the single continuous sealing protrusion form a sealing grid about the plurality of reservoirs.

21 Claims, 4 Drawing Sheets

Related U.S. Application Data

(60) Provisional application No. 61/527,482, filed on Aug. 25, 2011.

(51) Int. Cl.
*A61B 5/00* (2006.01)
*A61K 9/00* (2006.01)
*A61B 5/07* (2006.01)

(52) U.S. Cl.
CPC .................. *A61B 2562/168* (2013.01); *A61M 2205/0244* (2013.01); *A61M 2207/00* (2013.01); *B01L 2200/0689* (2013.01); *B01L 2200/12* (2013.01); *B01L 2300/042* (2013.01); *B01L 2300/0819* (2013.01); *B01L 2300/0848* (2013.01); *B01L 2300/0858* (2013.01); *B01L 2300/12* (2013.01); *Y10T 29/49126* (2015.01)

(56) References Cited

U.S. PATENT DOCUMENTS

| | | |
|---|---|---|
| 6,123,861 A | 9/2000 | Santini, Jr. et al. |
| 6,491,666 B1 | 12/2002 | Santini, Jr. et al. |
| 6,527,762 B1 | 3/2003 | Santini, Jr. et al. |
| 6,551,838 B2 | 4/2003 | Santini, Jr. et al. |
| 6,773,429 B2 | 8/2004 | Sheppard, Jr. et al. |
| 6,808,522 B2 | 10/2004 | Richards et al. |
| 6,827,250 B2 | 12/2004 | Uhland et al. |
| 6,875,208 B2 | 4/2005 | Santini, Jr. et al. |
| 6,976,982 B2 | 12/2005 | Santini, Jr. et al. |
| 7,070,590 B1 | 7/2006 | Santini, Jr. et al. |
| 7,114,312 B2 | 10/2006 | Coppeta et al. |
| 7,226,442 B2 | 6/2007 | Sheppard, Jr. et al. |
| 7,323,142 B2 | 1/2008 | Pendo et al. |
| 7,354,597 B2 | 4/2008 | Johnson et al. |
| 7,413,846 B2 | 8/2008 | Maloney et al. |
| 7,488,316 B2 | 2/2009 | Prescott et al. |
| 7,497,855 B2 | 3/2009 | Ausiello et al. |
| 7,510,551 B2 | 3/2009 | Uhland et al. |
| 7,534,241 B2 | 5/2009 | Coppeta et al. |
| 7,537,590 B2 | 5/2009 | Santini, Jr. et al. |
| 7,599,737 B2 | 10/2009 | Yomtov et al. |
| 7,604,628 B2 | 10/2009 | Santini, Jr. et al. |
| 7,916,013 B2 | 3/2011 | Stevenson |
| 7,917,208 B2 | 3/2011 | Yomtov et al. |
| 8,095,197 B2 | 1/2012 | Santini, Jr. et al. |
| 8,191,756 B2 | 6/2012 | Coppeta et al. |
| 8,374,698 B2 | 2/2013 | Ok et al. |
| 2002/0119176 A1 | 8/2002 | Greenberg et al. |
| 2002/0187260 A1 | 12/2002 | Sheppard et al. |
| 2003/0034564 A1 | 2/2003 | Palanisamy et al. |
| 2004/0106953 A1 | 6/2004 | Yomtov et al. |
| 2004/0247671 A1 | 12/2004 | Prescott et al. |
| 2005/0267440 A1 | 12/2005 | Herman et al. |
| 2006/0076236 A1 | 4/2006 | Shah et al. |
| 2006/0115323 A1 | 6/2006 | Coppeta et al. |
| 2008/0217752 A1* | 9/2008 | Hata .................. B81C 1/00269 257/686 |
| 2008/0302659 A1 | 12/2008 | Sheppard, Jr. et al. |
| 2010/0119604 A1 | 5/2010 | Prescott et al. |
| 2010/0148293 A1 | 6/2010 | Jain et al. |
| 2010/0149042 A1 | 6/2010 | Utsi et al. |
| 2011/0089957 A1 | 4/2011 | Sheppard, Jr. et al. |
| 2011/0270067 A1 | 11/2011 | Faraji et al. |
| 2012/0035528 A1 | 2/2012 | Copetta et al. |
| 2012/0130339 A1 | 5/2012 | Farra |

\* cited by examiner

SYSTEMS AND METHODS FOR SEALING A PLURALITY OF RESERVOIRS OF A MICROCHIP ELEMENT WITH A SEALING GRID

CROSS-REFERENCE TO RELATED APPLICATIONS

This is a continuation-in-part of U.S. application Ser. No. 13/595,492, filed Aug. 27, 2012, which claims priority to and the benefit of U.S. provisional application No. 61/527,482, filed Aug. 25, 2011. Those applications are incorporated herein by reference.

FIELD OF THE DISCLOSURE

This disclosure generally relates to containment devices, including but not limited to medical devices, such as implantable medical devices, having one or more microchip elements having a plurality of containment reservoirs for hermetically confining substance or subcomponents for later exposure or release. In particular, this disclosure relates to improved microchip elements and methods of manufacture thereof, including structures for sealing a plurality of reservoirs in a space-efficient assembly.

BACKGROUND

Microchips Biotech Inc. designs and manufactures implantable devices based on microchips which include reservoir arrays containing biosensors or drugs. FIG. 1 shows a plan view of sealing grooves and reservoirs in a microchip element 100. The microchip element 100 includes a primary substrate 102 with reservoirs 104, such as microreservoirs. Each reservoir may contain a drug or sensor (neither of which is shown, for simplicity) for controlled in vivo release or exposure, respectively. In order to form a hermetic enclosure about the reservoirs 104, the primary substrate 102 is bonded to a sealing substrate. In this manner, the primary substrate 102 typically includes a number of discrete sealing rings 106 disposed about each individual reservoir 104. The individual sealing rings 106, however, occupy a substantial portion of the surface area of the microchip element 100 and therefore limit the size of the reservoirs 104 and/or limit how closely the reservoirs can be positioned next to one another. That is, the arrangement limits how densely the reservoirs can be packed together in an array. A high density is desirable because it leads to more reservoirs and reservoir contents per volume of the medical implant, and the smaller the medical implant the more tolerable the implanted device is to the patient. It therefore would be desirable to increase the reservoir capacity or area density, while still providing a hermetic seal about the reservoirs and without needing to increase the overall size of the microchip element. It would also be desirable to simplify the fabrication of the sealing structures needed to hermetically seal reservoirs in an array of reservoirs in a microchip element.

SUMMARY

Systems and methods for sealing a plurality of reservoirs of a microchip element with a sealing grid are provided. For example, in one embodiment, a microchip element comprises a primary substrate having a plurality of reservoirs defined therein. The microchip element also includes a single continuous sealing groove defined in the primary substrate that extends around each of the plurality of reservoirs. In addition, the microchip element includes a sealing substrate comprising a single continuous sealing protrusion extending therefrom. The single continuous sealing protrusion corresponds to and is configured to mate with the single continuous sealing groove to form a hermetic bond between the primary substrate and the sealing substrate. In this manner, the single continuous sealing groove and the single continuous sealing protrusion form a sealing grid about the plurality of reservoirs.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

The microchip element described herein advantageously improves significantly the space efficiency of the device by providing interconnected, or shared, hermetic seals between and among the reservoirs in an array of containment reservoirs. This sharing may be accomplished with a single continuous protrusion bonded with a corresponding single continuous groove. By designing the hermetic seals between substrate portions (sealing the containment reservoirs) to be formed by mating shared rings (i.e., protruding features) and grooves around each reservoir, the microchip elements advantageously are able to have increased reservoir capacity and/or increased packing density of the reservoirs in an array of containment reservoirs. That is, as compared to a device in which each of the reservoirs in an array has its own independent sealing ring, more and/or larger reservoirs can be provided in a same device dimensions. The is highly beneficial, as it is important to patients' comfort to keep the size of the medical implant as small as possible while at the same time maximizing the volume of space in the device available for containing drug payload, sensors, or other reservoir components.

The microchip element described herein may be incorporated into various containment device systems and assemblies, in particular implantable medical devices for drug delivery and/or biosensing. For example, the microchip element may be incorporated into the implant devices and assemblies described in U.S. patent application publications No. 2013/0053671 A1, No. 2014/0180262 A1, and No. 2014-0243624 A1, which are incorporated herein by reference.

Figure 1:
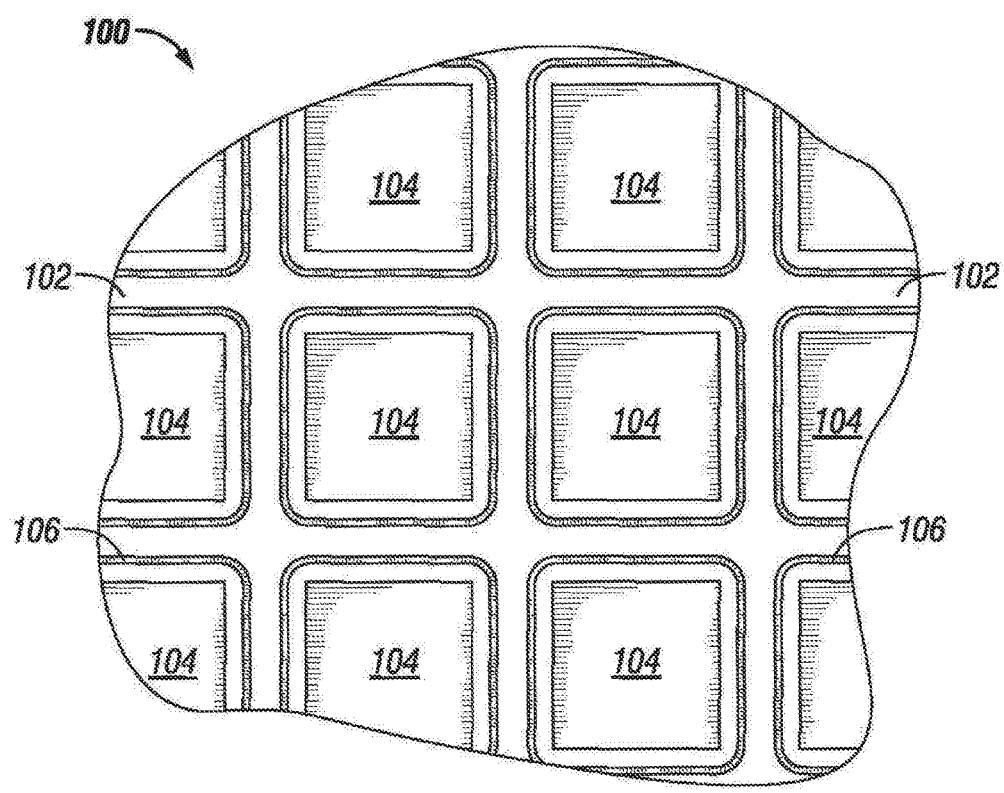
FIG. 1 is a top view of a portion of a prior art microchip element.
Figure 2A:
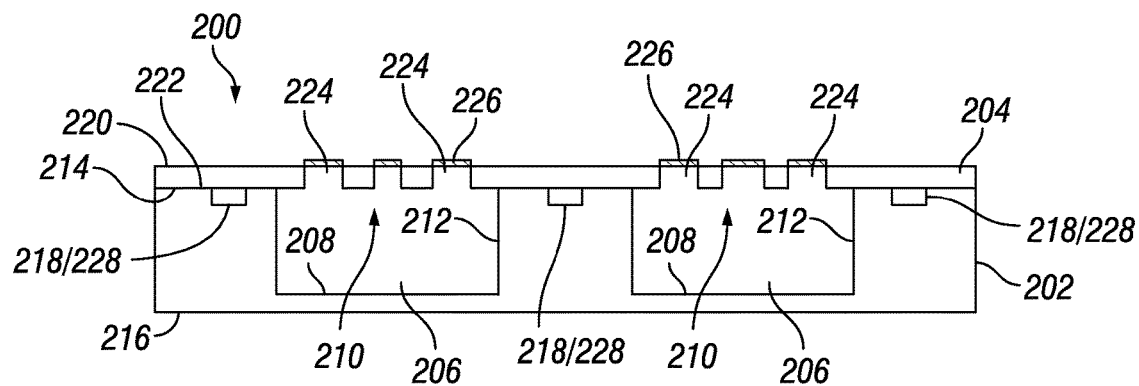
FIG. 2A is a cross-sectional view of a microchip element assembly according to an embodiment.
Figure 2B:
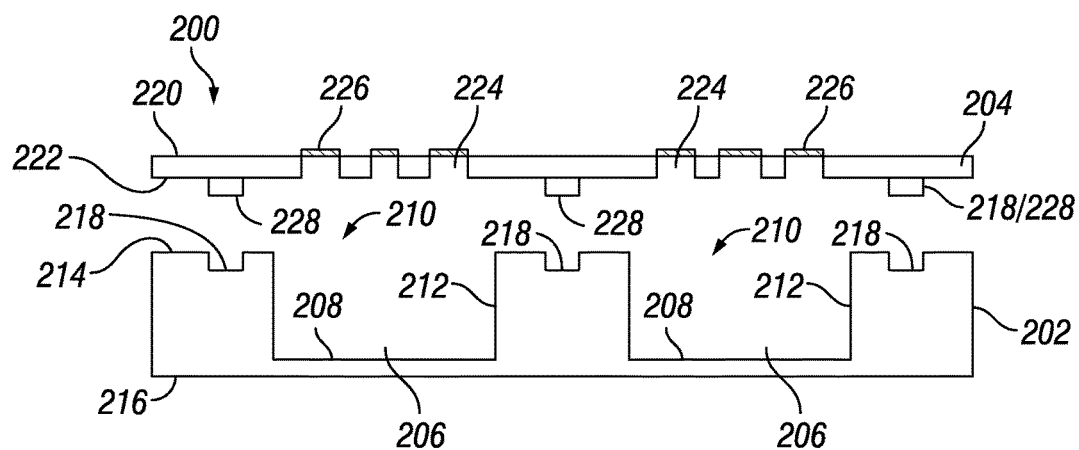
FIG. 2B is an exploded cross-sectional view of the microchip element assembly shown in FIG. 2A.

An exemplary embodiment of a microchip element 200 is illustrated in FIGS. 2A and 2B. The microchip element 200 includes a primary substrate 202 and a sealing substrate 204, which are bonded together. The primary substrate 202 includes a plurality of reservoirs 206. Each reservoir 206 is defined by a closed end wall 208, an open end 210, and at least one sidewall 212 extending between the closed end wall 208 and the open end 210. The primary substrate 202 includes a first side 214 and an opposed second side 216. In some instances, the open end 210 of the reservoir 206 is disposed about the first side 214 of the primary substrate 202.

The primary substrate 202 includes a sealing groove 218. The sealing groove 218 is disposed in the first side 214 of the primary substrate 202 between the reservoirs 206. In some instances, the sealing groove 218 is disposed between and shared by at least two of the reservoirs 206. That is, two different reservoirs share the same groove and are disposed on each side of the groove. In certain embodiments, the sealing groove 218 comprises a single continuous sealing groove 218 that extends around and is be shared by at least two or more of the reservoirs 206. In some instances, the single continuous sealing groove 218 may extend around and be shared by all of the reservoirs 206. For example, the single continuous sealing groove 218 may extend about the reservoirs 206 along a perimeter of the microchip element 200 and in-between the reservoirs 206 within an interior of the microchip element 200. In this manner, at least a portion of the single continuous sealing groove 218 is directly bordered on each side by a reservoir 206 without any intervening components, such as a separate sealing ring groove. The single continuous sealing groove 218 may be U-shaped, with square or rounded edges. In addition, the single continuous sealing groove 218 may include chamfered edges or the like. The single continuous sealing groove 218 may be any size, shape, or configuration.

In some instances, the primary substrate 202 is formed of a polymer or a glass or other ceramic material by any suitable process, including but not limited to molding, casting, micromachining, and build-up or lamination techniques known in the art. In one embodiment, the primary substrate 202 is made of/by low temperature co-fired ceramics (LTCC). It may further include a coating layer on all or a portion of the substrate, for example to provide or improve hermeticity, biocompatibility, bonding, and/or reservoir content compatibility, stability, or release. Depending on the purpose of the coating layer, it may be applied inside the reservoirs, outside of the reservoirs, or both. Examples of possible coating materials include biocompatible metals, such as gold, and polymers, such as parylene.

In some instances, the sealing substrate 204 is a silicon substrate or the like. The sealing substrate 204 has a first side 220, an opposed second side 222, and apertures 224 extending therethrough. Three apertures 224 are shown for each reservoir 206. Any number of apertures 224, however, may be associated with each reservoir 206. The first side 220 of the sealing substrate 204 includes one or more reservoir caps 226 which close off the apertures 224 until the reservoir 206 needs to be opened. In a preferred embodiment, the reservoir caps 226 are electrically conductive. For example, the reservoir caps 226 may be in the form of a metal film.

The sealing substrate 204, the apertures 224, and the reservoir caps 226 can be made using microfabrication techniques known in the art. For example, the photolithography, etching, and deposition techniques described in U.S. Pat. No. 7,604,628 may be used to form the apertures in a polysilicon substrate closed off by metal reservoir caps. Any fabrication techniques may be used herein.

The sealing substrate 204 may include a sealing protrusion 228. The sealing protrusion 228 may extend from the second side 222 of the sealing substrate 204. The sealing protrusion 228 may correspond to and be configured to mate with the sealing groove 218 on the first side 214 of the primary substrate 202. In some instances, the sealing protrusion 228 may be a single continuous sealing protrusion 228. In this manner, the single continuous sealing protrusion 228 may extend from the second side 222 of the sealing substrate 204 around and between the reservoirs 206 in the primary substrate 202 and mate with the single continuous sealing groove 218. That sealing protrusion 218 may be any size, shape, or configuration suitable to mate with and form a seal with the sealing groove 218. For example, the sealing protrusion 218 may be a single continuous block shaped structure.

The primary substrate 202 and the sealing substrate 204 are bonded together using any suitable method, to hermetically seal the reservoirs 206. In this way, the open end 210 of the reservoir 206 is in fluid communication with the apertures 224 for controlled release or exposure of reservoir contents. In a preferred embodiment, the substrates are hermetically sealed together using a compression cold welding process, such as described in U.S. Pat. No. 8,191,756, which is incorporated herein by reference. For example, as noted above, the second side 222 of the sealing substrate 204 includes a single continuous sealing protrusion 228 formed thereon, and the first side 214 of the primary substrate 202 includes a single continuous sealing groove 218. These bonding features are compressed together to form a cold weld bond, a hermetic seal, surrounding the individual reservoirs. The single continuous sealing protrusion 228 may be formed by a depositing gold or another metal layer on the sealing substrate 204. The single continuous sealing groove 218 may be etched in the silicon and then coated with a metallized layer of the same material as the single continuous sealing protrusion 228. Variations of this embodiment are envisioned, for example, where other positive and negative bonding features are provided in/on either or both interfacing surfaces of the sealing substrate 204 and the primary substrate 202. The arrangement of the single continuous sealing protrusion 228 and the single continuous sealing groove 218 may be reversed. For example, the sealing substrate 204 may include the single continuous sealing groove 218, and the primary substrate 202 may include single continuous sealing protrusion 228. In addition, the sealing substrate 204 may include the reservoirs 206, and/or the primary substrate 202 may include the apertures 224 and reservoir caps 226. In this manner, the various components of the microchip element 200 described above may be disposed on, within, or formed by the primary substrate 202, the sealing substrate 204, or a combination thereof.

Figure 3B:
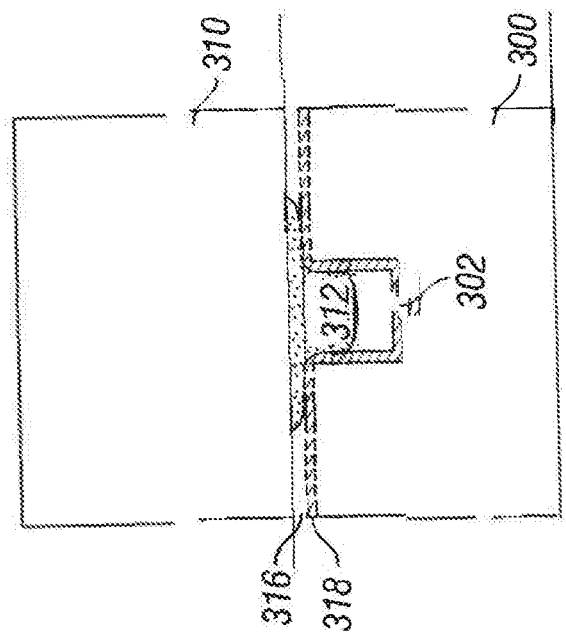
FIG. 3B is a cross-sectional view of a microchip element assembly shown in FIG. 3A after being bonded together.
Figure 3A:
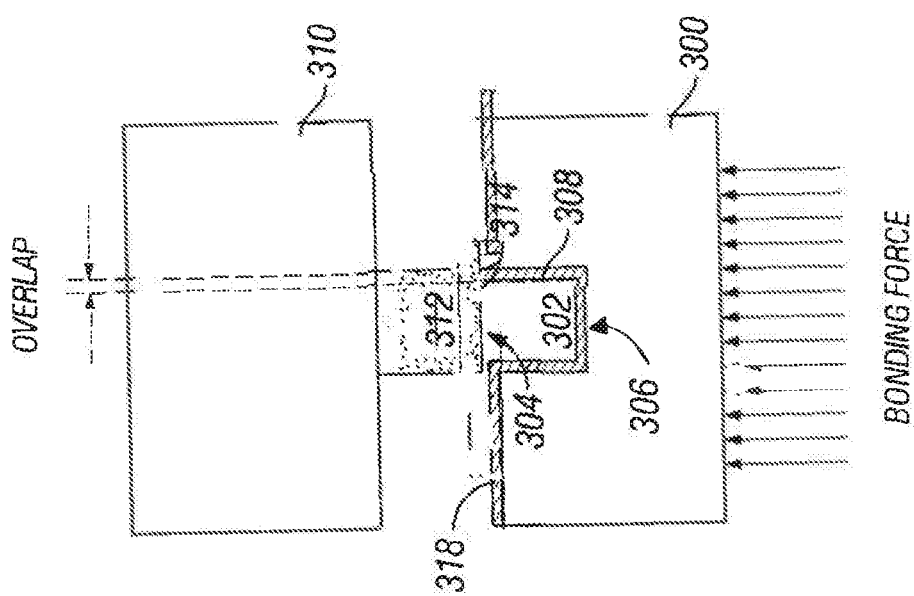
FIG. 3A is a cross-sectional view of a microchip element assembly according to an embodiment.

In one embodiment, as depicted in FIGS. 3A and 3B, the method of hermetically sealing the substrates together includes (i) providing a first substrate 300 which has the continuous groove 302 defined therein and wherein the groove 302 has an open end 304, and an inner bottom surface 306 distal to the open end 304, and inner side walls 308 between the open end 304 and the inner bottom surface 306; (ii) providing a second substrate 310 which has the continuous protrusion structure 312, wherein the protrusion structure 312 has a tip end portion 314; (iii) aligning the continuous groove 302 and the continuous protrusion 312 in a facing relationship, wherein the alignment and/or the relative dimensions of the groove 302 and protrusion 312 structures form an area of overlap (e.g., such that upon compression the protrusion 312 cannot fit completely within the groove 302 without some shearing and plastic deformation of an edge portion of the protrusion 312); (iv) and then compressing the protrusion 312 at least partially into the groove 302 to locally deform and shear the structures, at one or more interfaces created by the overlap, in an amount effective to plastically deform a portion of protrusion 312 into a space 316 between the first 300 and second 310 substrates outside of the groove structure 302 and to form a metal-to-metal bond (cold weld) between metal surfaces 318 of the two substrates. The metal-to-metal bond is a cold weld which comprises a portion of the protrusion 312 that has been plastically deformed into the space 316 between the first substrate 300 and the second substrate 310 outside of the continuous groove 302. The shearing and deformation are effective to displace surface contaminants and facilitate intimate contact between the joining surfaces without heat input. In preferred embodiments, the tip end portion 314 of the continuous protrusion 312 does not extend far enough into the continuous groove 302 to contact the inner bottom surface 306 of the continuous groove 302.

In embodiments, the protrusion has a height ranging from 1 micron to 100 microns and a width ranging from 1 micron to 100 microns, and the groove has a depth ranging from 1 micron to 100 microns and a width ranging from 1 micron to 100 microns.

The primary substrate 202 is generally relatively thicker than sealing substrate 204, and all or at least a majority (greater than 50%) of the reservoir sidewall height (or depth) is define by the primary substrate 202. In an embodiment, the sealing substrate 204 has thickness that is between 5% and 50% of the thickness of the primary substrate 202 at the bonded interfaces of the substrates.

Although not shown in the FIGS. 2A and 2B, some or all of the reservoirs 206 include reservoir contents positioned therein. The reservoirs 206 can be configured to store essentially any substance or device component in need hermetic containment and subsequent release or exposure at a selected time. The reservoir content may be, for example, a chemical reagent, a drug formulation, or sensor or component thereof, such as an electrode. In an embodiment, a single microchip element includes a plurality of reservoirs, some of which contain a biosensor and other that contain a drug formulation. Examples of various reservoir contents are described for example in U.S. Pat. Nos. 7,510,551; 7,497,855; 7,604,628; 7,488,316; and PCT WO 2012/027137.

Figure 4:
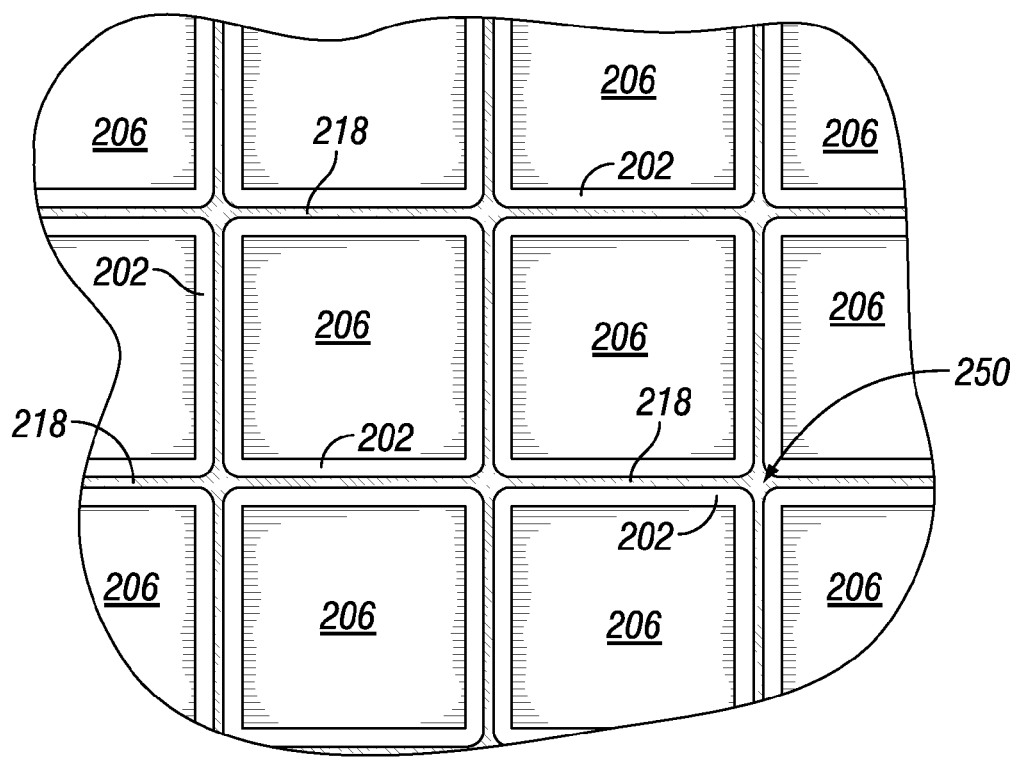
FIG. 4 is a top view of a portion of a microchip element including a sealing grid according to an embodiment.

FIG. 4 depicts a portion of the primary substrate 202 with a sealing grid 250. The sealing grid 250 includes the single continuous sealing groove 218. As depicted in FIG. 4, the single continuous sealing groove 218 extends around and between all of the reservoirs 206. In this manner, as its name implies, the single continuous sealing groove 218 is a continuous groove that surrounds each of the reservoirs 206 as a single, uninterrupted channel. The sealing grid 250 eliminates the need for individual sealing rings about each reservoir of the microchip element by consolidating all of the sealing rings into a single continuous groove that surrounds each of the reservoirs 206 as an uninterrupted channel. By eliminating the individual sealing rings, the size and capacity of the reservoirs may be increased. For example, prior microchip elements having individual sealing rings about each reservoir may include reservoir width and length dimensions of 1 mm×1 mm. By using a single continuous sealing grid 250, however, the reservoir width and length dimensions may be increased to 1.21 mm×1.21 mm without increasing the overall size of the microchip element 200. The reservoirs 206 may be any size, shape, or configuration.

The single continuous sealing protrusion 228 may be disposed on the sealing substrate 204. The single continuous sealing protrusion 228 may include an identical pattern as the single continuous sealing groove 218 such that it may be cold welded to the single continuous sealing groove 218 when the sealing substrate 204 is hermetically bonded to the primary substrate 202. That is, the single continuous sealing protrusion 228 and the single continuous sealing groove 218 are compressed together to form a cold weld bond, a hermetic seal, surrounding the individual reservoirs 206.

The term "biocompatible" as used herein generally refers to materials of construction that are suitable for long-term implantation into a human or animal subject, e.g., a patient. Such materials of constructions are known in the art of implantable medical devices. As used herein, the term "hermetic seal" refers to preventing undesirable ingress or egress of chemicals (e.g., water vapor, water, oxygen, etc.) into or from one or more compartments of the device, such as the device reservoirs, over the useful life of the device. For purposes herein, a material/seal that transmits helium (He) at a rate less than $1\times10^{-9}$ atm*cc/sec is termed hermetic.

It is understood that each microchip element may include a plurality of discrete reservoirs (e.g., from 10 to 750 reservoirs). Fewer or more reservoirs per device are also envisioned. The reservoirs 206 of the microchip element 200 may be configured to open/activate in a variety of ways, which may be known in the art. In one embodiment, the reservoirs are structured and configured to be electrically activated to open as described in U.S. Pat. Nos. 7,510,551 and 7,604,628, which are incorporated herein by reference.

In one embodiment, the reservoir caps 226 are structured and configured to be electrically activated to open as described in U.S. Pat. Nos. 7,510,551 and 7,604,628, which are incorporated herein by reference. The reservoir caps 226 may be formed of a metal film, which may comprise a single layer or a laminate structure. For example, the reservoir cap 226 may comprise gold, platinum, titanium, or a combination thereof. In other embodiments, the reservoir cap 226 can be configured to be activated or opened by a mechanical mechanism or electrochemical mechanisms.

The reservoirs 206 of the microchip element 200 may be "microreservoirs," which generally refers to a reservoir having a volume equal to or less than 500 nL (e.g., less than 250 nL, less than 200 nL, less than 50 nL, less than 25 nL, less than 10 nL, etc.). In another embodiment, the reservoirs 206 are "macroreservoirs," which generally refers to a reservoir having a volume greater than 500 nL (e.g., greater than 600 nL, greater than 750 nL, greater than 900 nL, greater than 1 µL, etc.) and less than 50 µL (e.g., less than 40 µL, less than 20 µL, less than 4 µL, less than 3 µL, less than 2 µL, less than 1 µL, etc.). The terms "reservoir" and "containment reservoir" are intended to encompass both microreservoirs and macroreservoirs unless explicitly indicated to be limited to either one or the other.

In a second aspect, improved microchip elements and methods for their manufacture are provided. In a preferred embodiment, the microchip device element includes a relatively thin sealing (e.g., silicon) substrate bonded to a relatively thicker primary substrate formed of a polymer or a glass or other ceramic material. Advantageously, by defining the reservoirs in the primary substrate rather than the silicon substrate, the reservoirs may be formed using processes other than dry reactive ion etching (DRIE). This is important, not just because DRIE processes are expensive, but also because under the conventional process, the DRIE processes occurred after deposition of the reservoir cap film, unnecessarily exposing the reservoir cap film to subsequent processing, which can negatively impact the yield of acceptable (e.g., hermetic) reservoir caps.

In addition, by adding the positive sealing features (e.g., the single continuous sealing protrusion) to the silicon substrate, this keeps all of the high tolerance microfeatures to only the silicon substrate, which in turn frees up the primary substrate to be made by other, potentially lower tolerance, manufacturing processes. In this way, the reservoir can be made much deeper and thereby increase the unit reservoir payload. In one embodiment, the primary substrate is made by a casting or molding process using ceramic or polymeric materials that allows for formation of reservoirs that are deeper than conventional reservoirs and having smoother side walls than would be readily possible using DRIE. This cast or molded substrate then may be gold plated in and about sealing grooves formed therein for bonding with the positive sealing features on the silicon substrate.

Modifications and variations of the methods and devices described herein will be obvious to those skilled in the art from the foregoing detailed description. Such modifications and variations are intended to come within the scope of the appended claims.

Although specific embodiments of the disclosure have been described, numerous other modifications and alternative embodiments are within the scope of the disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

I claim:

1. A microchip element, comprising:
a primary substrate comprising a plurality of reservoirs defined therein;
a single continuous sealing groove defined in the primary substrate and extending between and shared by all of the plurality of reservoirs; and
a sealing substrate comprising a single continuous sealing protrusion extending therefrom,
wherein the single continuous sealing protrusion corresponds to and is configured to mate with the single continuous sealing groove to form a hermetic bond between the primary substrate and the sealing substrate,
wherein the single continuous groove and the single continuous sealing protrusion extend around and are shared by each of the plurality of reservoirs, such that each reservoir does not have its own independent sealing ring,
wherein each of the plurality of reservoirs is defined by a closed end wall, an open end, and at least one sidewall extending between the closed end wall and the open end, and
wherein the sealing substrate comprises a first side, an opposed second side, and a plurality of apertures extending therethrough, wherein the first side comprises a plurality of electrically conductive reservoir caps which close off the plurality of apertures.

2. The microchip element of claim 1, wherein the single continuous sealing protrusion is disposed on the second side of the sealing substrate, and wherein the second side of the sealing substrate is hermetically bonded to the primary substrate, such that the open end of the plurality of reservoirs is in fluid communication with at least one aperture of the plurality of apertures.

3. The microchip element of claim 1, wherein the sealing substrate comprises a silicon substrate.

4. The microchip element of claim 1, wherein the primary substrate comprises a polymer or a glass or other ceramic material.

5. The microchip element of claim 4, wherein the primary substrate comprises a metal coating over at least a part of the polymer, glass or other ceramic material of the primary substrate.

6. The microchip element of claim 5, wherein the metal coating coats the at least one sidewall and/or the closed end wall of each of the plurality of reservoirs.

7. The microchip element of claim 1, further comprising reservoir contents positioned within at least one reservoir of the plurality of reservoirs.

8. The microchip element of claim 1, wherein the single continuous sealing protrusion comprises gold.

9. The microchip element of claim 1, wherein the single continuous sealing groove comprises gold.

10. The microchip element of claim 1, wherein the closed end wall and the at least one sidewall are part of the same monolithic structure.

11. The microchip element of claim 1, wherein the plurality of reservoirs comprise a drug payload.

12. A microchip element, comprising:
a sealing substrate;
a primary substrate;
a plurality of reservoirs defined within the primary substrate and/or within the sealing substrate;
a sealing grid comprising a single continuous sealing groove and a single continuous sealing protrusion, wherein the single continuous groove and the single continuous sealing protrusion extend around and are shared by each of the plurality of reservoirs; and
wherein the single continuous sealing protrusion corresponds to and is configured to mate with the single continuous sealing groove to form a hermetic bond between the primary substrate and the sealing substrate,
wherein each reservoir does not have its own independent sealing ring,
wherein each of the plurality of reservoirs is defined by a closed end wall, an open end, and at least one sidewall extending between the closed end wall and the open end, and
wherein the sealing substrate comprises a first side, an opposed second side, and a plurality of apertures extending therethrough, wherein the first side comprises a plurality of electrically conductive reservoir caps which close off the plurality of apertures.

13. The microchip element of claim 12, wherein the single continuous sealing protrusion is disposed on the second side of the sealing substrate, and wherein the second side of the sealing substrate is hermetically bonded to the primary substrate, such that the open end of the plurality of reservoirs is in fluid communication with at least one aperture of the plurality of apertures.

14. The microchip element of claim 12, further comprising reservoir contents positioned within at least one reservoir of the plurality of reservoirs.

15. The microchip element of claim 1, wherein the closed end wall and the at least one sidewall are part of the same monolithic structure.

16. The microchip element of claim 12, wherein the single continuous groove and the single continuous sealing protrusion form interconnected squares with rounded corners, each square being around one of the reservoirs.

17. The microchip element of claim 12, wherein the plurality of reservoirs comprise a drug payload.

18. The microchip element of claim 12, wherein the at least one sidewall of each reservoir has a height which is defined more than 50% by the primary substrate.

19. The microchip element of claim 12, wherein the plurality of reservoirs are microreservoirs.

20. An implantable medical device comprising:
an array of hermetically sealed reservoirs defined by two substrate portions which are bonded together by a single continuous protrusion mated with a single continuous groove, which surrounds each of the hermetically sealed reservoirs,
wherein the mated single protrusion and single groove extend around and are shared by each of the hermetically sealed reservoirs, and each of the hermetically sealed reservoirs does not have its own independent sealing ring,
wherein each of the hermetically sealed reservoirs is defined by a closed end wall, an open end, and at least one sidewall extending between the closed end wall and the open end, and
wherein a sealing substrate of the two substrate portions comprises a first side, an opposed second side, and a plurality of apertures extending therethrough, wherein the first side comprises a plurality of electrically conductive reservoir cap which close off the plurality of apertures.

21. The device of claim 20, wherein the hermetically sealed reservoirs comprise a drug or a biosensor.

* * * * *